US008939886B2

(12) United States Patent
Chu

(10) Patent No.: US 8,939,886 B2
(45) Date of Patent: *Jan. 27, 2015

(54) SYSTEMS, METHODS AND DEVICES RELATING TO A REMOVABLE SLEEVE FOR AN IMPLANTABLE SLING

(75) Inventor: Michael S. H. Chu, Brookline, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/965,496

(22) Filed: Dec. 10, 2010

(65) Prior Publication Data

US 2011/0144422 A1 Jun. 16, 2011

Related U.S. Application Data

(63) Continuation of application No. 11/202,554, filed on Aug. 11, 2005, now Pat. No. 7,935,046.

(51) Int. Cl.
*A61F 2/02* (2006.01)
*A61F 2/00* (2006.01)

(52) U.S. Cl.
CPC .................................. *A61F 2/0045* (2013.01)
USPC ............................................................ 600/30

(58) Field of Classification Search
USPC ................... 600/29, 30, 37; 606/151; 128/885
See application file for complete search history.

(56) References Cited

U.S. PATENT DOCUMENTS

| 5,443,483 | A * | 8/1995 | Kirsch | 606/74 |
| 5,599,311 | A * | 2/1997 | Raulerson | 604/175 |
| 7,935,046 | B2 * | 5/2011 | Chu | 600/30 |
| 2002/0042658 | A1 * | 4/2002 | Tyagi | 623/23.72 |
| 2002/0156487 | A1 * | 10/2002 | Gellman et al. | 606/139 |

* cited by examiner

*Primary Examiner* — Christine Matthews

(57) ABSTRACT

Devices and methods for delivering of a sling assembly and removal of the sleeve at least partially enclosing the sling through a single orifice of incision are disclosed.

21 Claims, 12 Drawing Sheets

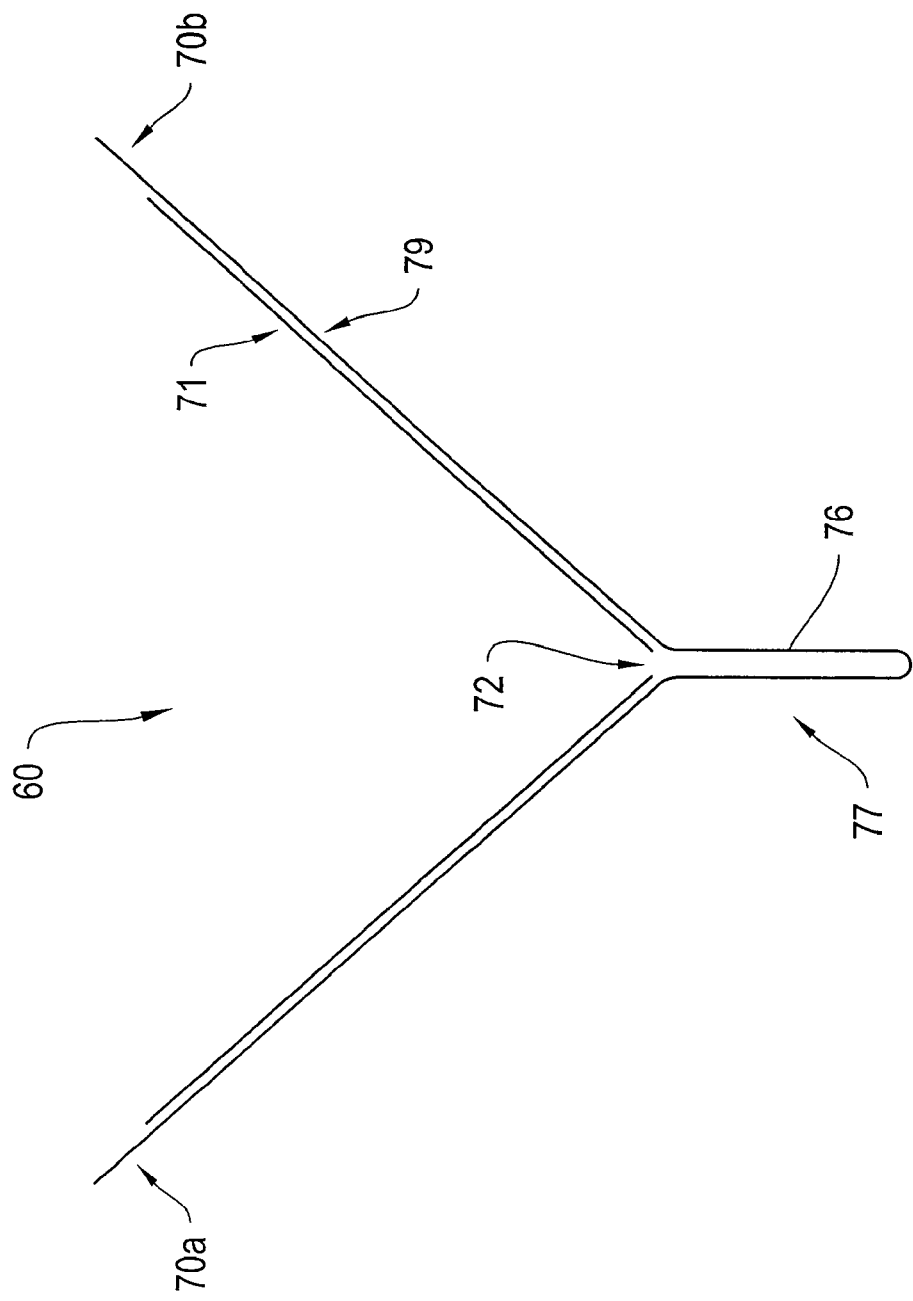

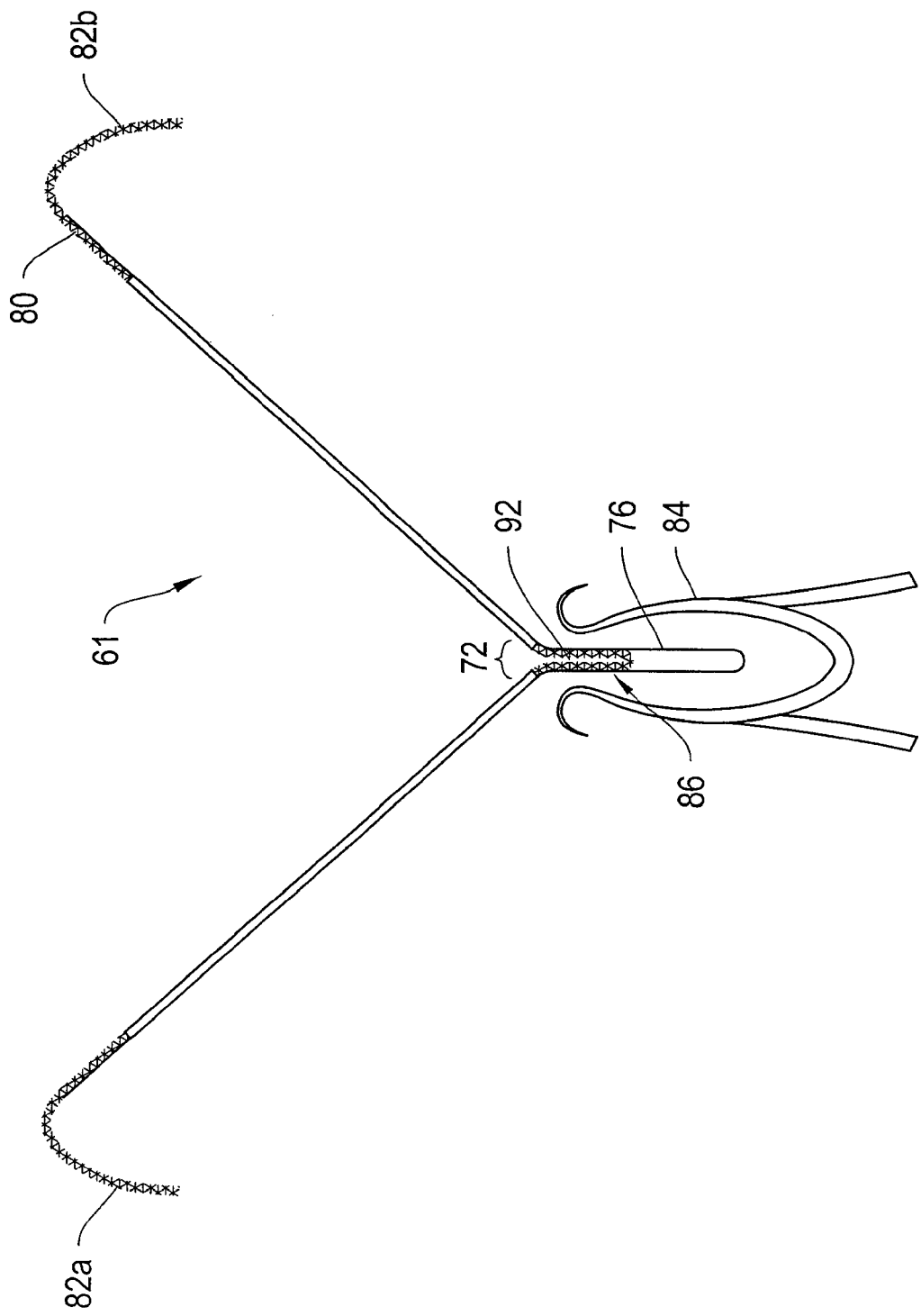

SYSTEMS, METHODS AND DEVICES RELATING TO A REMOVABLE SLEEVE FOR AN IMPLANTABLE SLING

This application is a continuation of U.S. application Ser. No. 11/202,554, filed Aug. 11, 2005, U.S. Pat No. 7,935,046 the disclosure of which is incorporated herein by reference in its entirety.

FIELD OF THE INVENTION

The invention generally relates to systems and methods for delivering a supportive sling to an anatomical location in a patient. More particularly, in various embodiments, the invention relates to systems and methods for delivering a supportive sling having an easily removable sleeve to the periurethral tissue of a patient to provide urethral support.

BACKGROUND OF THE INVENTION

Stress urinary incontinence (SUI) affects primarily women, but also men, and is generally caused by two conditions, intrinsic sphincter deficiency (ISD) and hypermobility. These conditions may occur independently or in combination. In ISD, the urinary sphincter valve, located within the urethra, fails to close properly (coapt), causing urine to leak out of the urethra during stressful activity. Hypermobilty is a condition in which the pelvis floor is distended, weakened or damaged, causing the bladder neck and proximal urethra to rotate and descend in response to increases in intra-abdominal pressure (e.g., due to sneezing, coughing, straining, etc.). As a result, the patient's response time becomes insufficient to promote urethral closure and, consequently, the patient suffers from urine leakage and/or flow.

A popular treatment of SUI uses a surgical sling placed under the bladder neck or the mid-urethra to provide a urethral platform. Placement of the sling limits the endopelvis fascia drop while providing compression to the urethral sphincter to improve coaptation. The mid-urethral sling is traditionally affixed using a bone anchoring method. Recent advances in surgical techniques have demonstrated the effectiveness of anchorless approaches toward mid-urethra sling stabilization. However, these anchorless techniques typically require incisions in addition to those made in the vaginal wall. By way of example, some procedures require abdominal incisions, while others require ishiopubic incisions.

Accordingly, there is a need for an improved approach to sling placement that simplifies the procedure and reduces trauma to the patient.

SUMMARY OF THE INVENTION

The invention addresses deficiencies of the prior art by, in one embodiment, providing systems, methods and devices for delivering a sling that is at least partially covered by an easily removable protective sleeve. According to one feature, the mechanism by which the protective sleeve is removed enables delivery of the sling through a single orifice, thereby eliminating the need for multiple incisions that cause unnecessary trauma to patients.

In one aspect, the invention provides a protective sleeve including a top layer, a bottom layer and first and second longitudinal edges. The top layer includes at least one portion having an longitudinally extending discontinuity forming at least a flap-like structure anchored along the first longitudinal edge of the sleeve. Preferably, the longitudinally extending discontinuity is located between the first and the second longitudinal edges of the sleeve, forming at least first and second flap-like structures, with the first flap-like structure anchored along the first longitudinal edge of the sleeve and the second flap-like structure anchored along the second longitudinal edge of the sleeve.

According to one embodiment, the top layer of the sleeve includes at least a first flapped section, a middle section and a second flapped section. Each of the first and the second flapped sections has a respective first longitudinally extending discontinuity forming a first flap-like structure in each flapped section. The first flap-like structure of each section is anchored along a longitudinal edge of the sleeve. According to one configuration, the middle section provides a gap on the top layer of the sleeve between the first and the second flapped sections. According to one configuration, the first longitudinally extending discontinuity of each flapped section is located along the longitudinal edge of the sleeve opposite the longitudinal edge providing the anchoring. In another configuration, the first longitudinally extending discontinuity of each flapped section is located between the first and the second longitudinal edges of the sleeve, forming first and second flap-like structures within each flapped section.

In a further embodiment, each of the first and the second flapped sections includes a transversely discontinuity extending between the first longitudinal edge and the opposing second longitudinal edge to divide each flap-like structure into at least two flap-like structures. The longitudinal ends of each of the flap-like structures may be of any suitable shape, such as straight, tapered, scallop-edged, fan-shaped or wavy.

According to another aspect of the invention, the bottom layer of the sleeve includes a first end tab at a first end of the sleeve and a second end tab at a second end of the sleeve. In one embodiment, the first end tab and the second end tab each comprises at least one through aperture for attaching to a delivery device. In an alternative embodiment, the first end tab and the second end tab each includes three through apertures, each of which is suitable for attaching to a delivery device.

According to another aspect of the invention, the sleeve includes a center tab located near a midpoint of the bottom layer of the sleeve. The center tab encloses a middle section of the bottom layer of the sleeve, and where appropriate, the middle-section of the top layer of the sleeve. In one embodiment, the center tab is formed by heat seal. In another embodiment, the center tab is formed by a clip.

In another aspect, the invention provides methods for delivering a sling at least partially covered by a sleeve of the invention to an anatomical site in a patient. The methods include positioning the sling at least partially covered by a sleeve near an anatomical site, and removing the sleeve from the sling by unfolding the sleeve transversely away from the sling to deliver the sling to the anatomical site.

In a further aspect, the invention provides methods for delivering a sling at least partially covered by a sleeve of the invention to an anatomical site in a patient through a single incision. The methods include placing a sling at least partially covered in a sleeve near the anatomical site through a single body orifice, and removing the sleeve away from the sling through the same body orifice to deliver the sling to the anatomical site.

Further features and advantages of the invention will be apparent from the following description of illustrative embodiments and from the claims.

BRIEF DESCRIPTION OF THE DRAWINGS

The following figures depict certain illustrative embodiments of the invention in which like reference numerals refer

FIG. 3B depicts a side view of the sleeve of FIG. 3A configured with a center tab formed from a looped middle section of the sleeve according to an illustrative embodiment of the invention;

FIG. 4B depicts a side view of the sling assembly of FIG. 4A with a center tab formed from a looped middle section of a bottom layer of the sleeve according to an illustrative embodiment of the invention;

ILLUSTRATIVE DESCRIPTION

In general, the invention is directed to systems and methods for the treatment of urinary incontinence. In one illustrative embodiment, the invention provides simplified devices and methods for delivering a supportive sling to an anatomical site of a patient, with reduced trauma to the patient. In a preferred embodiment, the supportive sling is sized and shaped for implantation the periurethral tissues of a patient to provide urethral support. According to one advantage, the devices and methods of the invention allow the placement of the sling and subsequent removal of a protective sleeve at least partially covering the sling through a single incision, thus eliminating the need for multiple incisions that cause unnecessary trauma to patients. According to another advantage, the devices and methods of the invention allow the removal of the sleeve from the sling without the need for cutting any part of the sleeve, further reducing unnecessary trauma to patients during a sling placement procedure. According to another advantage, the length of the sling is adjustable to accommodate people with varying distances between the urethra and the obturator. Depending on the patients, the length of the sling can be adjusted, for example, to maximize the length of the sling attached to the obturator foramen in patients to ensure maximum anchoring strength of sling to tissue. Examples of other adjustable slings are disclosed in commonly assigned U.S. Application No. 60/649,514 entitled "Systems and Methods Relating to Anchoring a Medical Implant to Tissue" and filed on Feb. 3, 2005, the contents of which are incorporated herein by reference in their entirety.

Figure 1A:
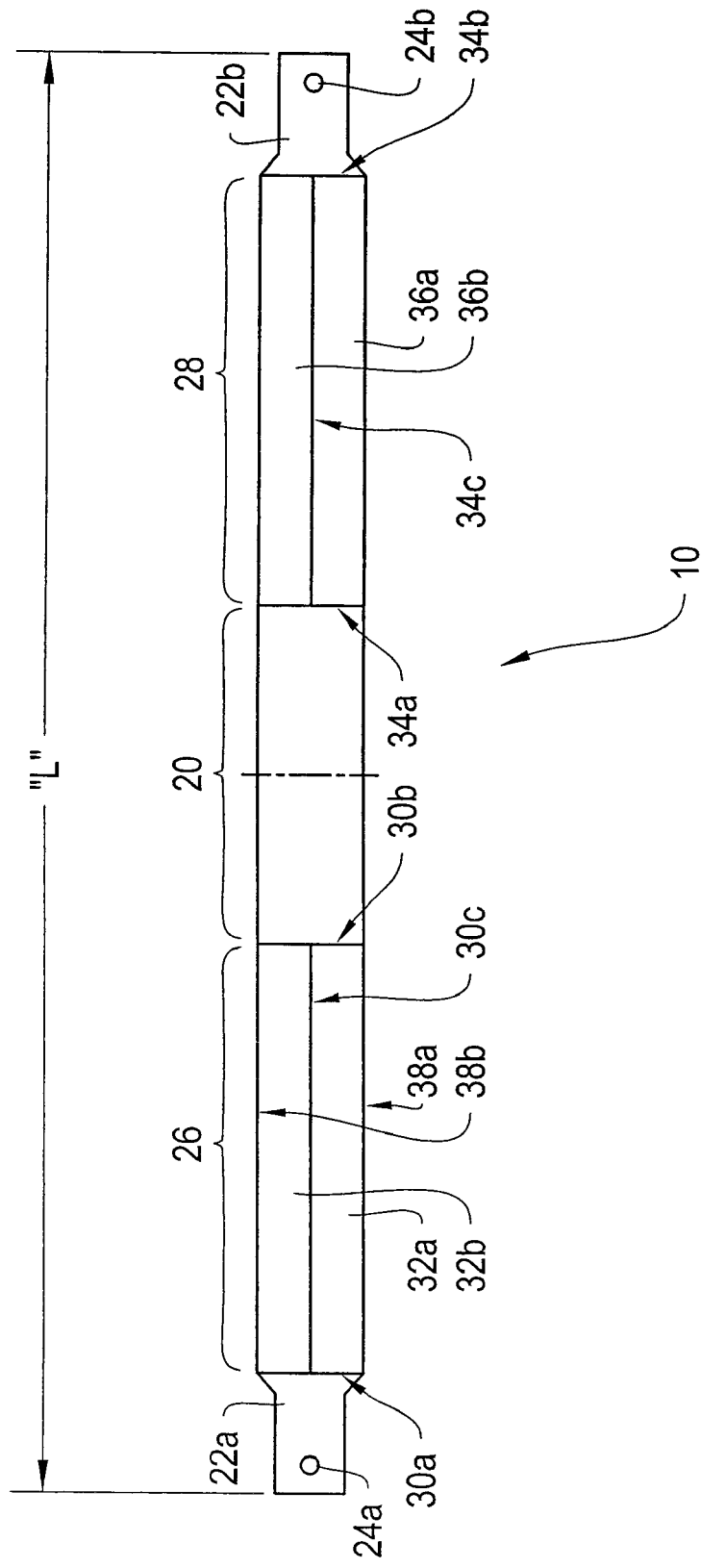
FIG. 1A depicts a top view of a removable sleeve in its full length according to an illustrative embodiment of the invention.
Figure 1B:
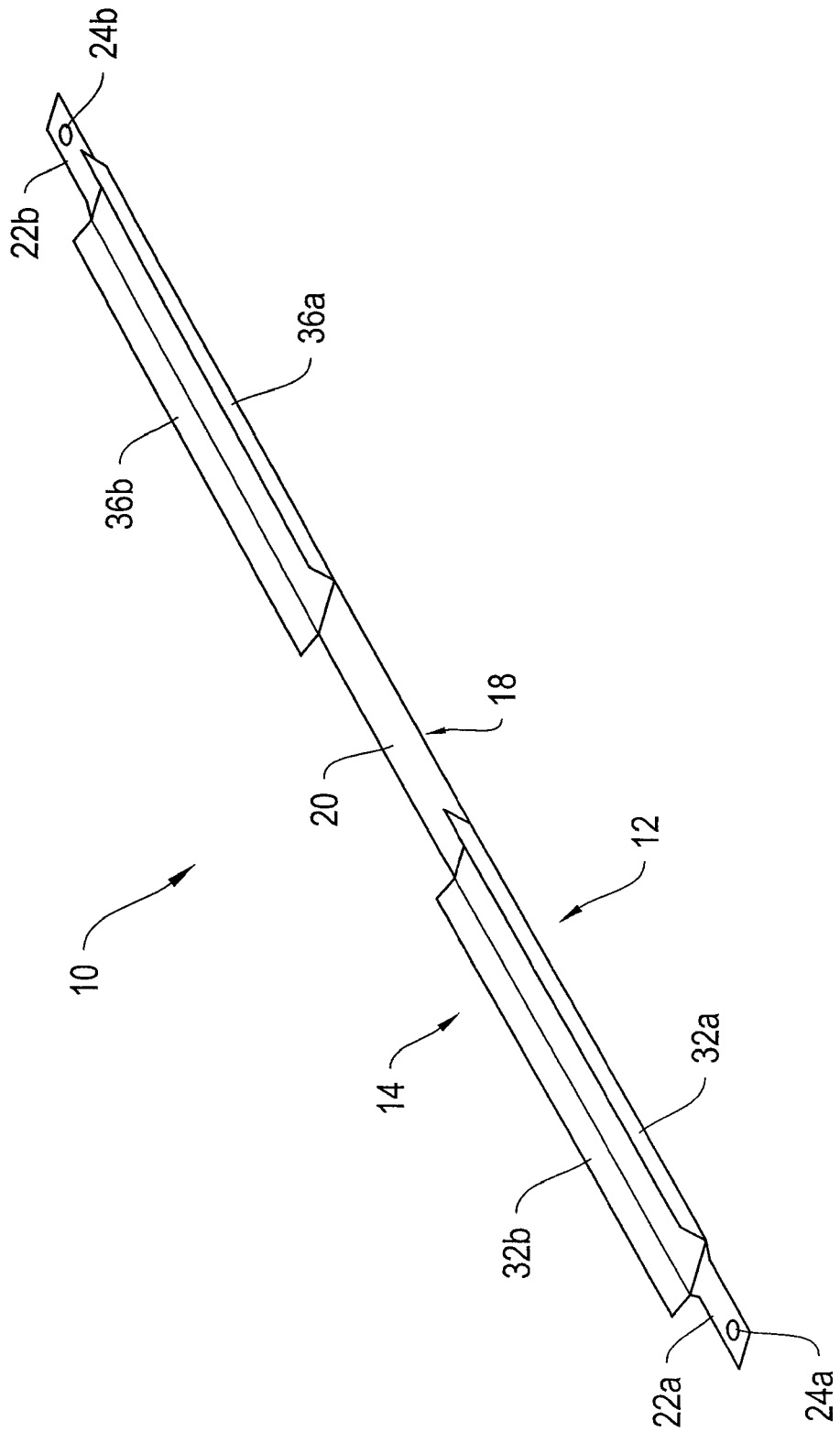
FIG. 1B depicts a perspective top view of the sleeve of FIG. 1A.
Figure 1C:
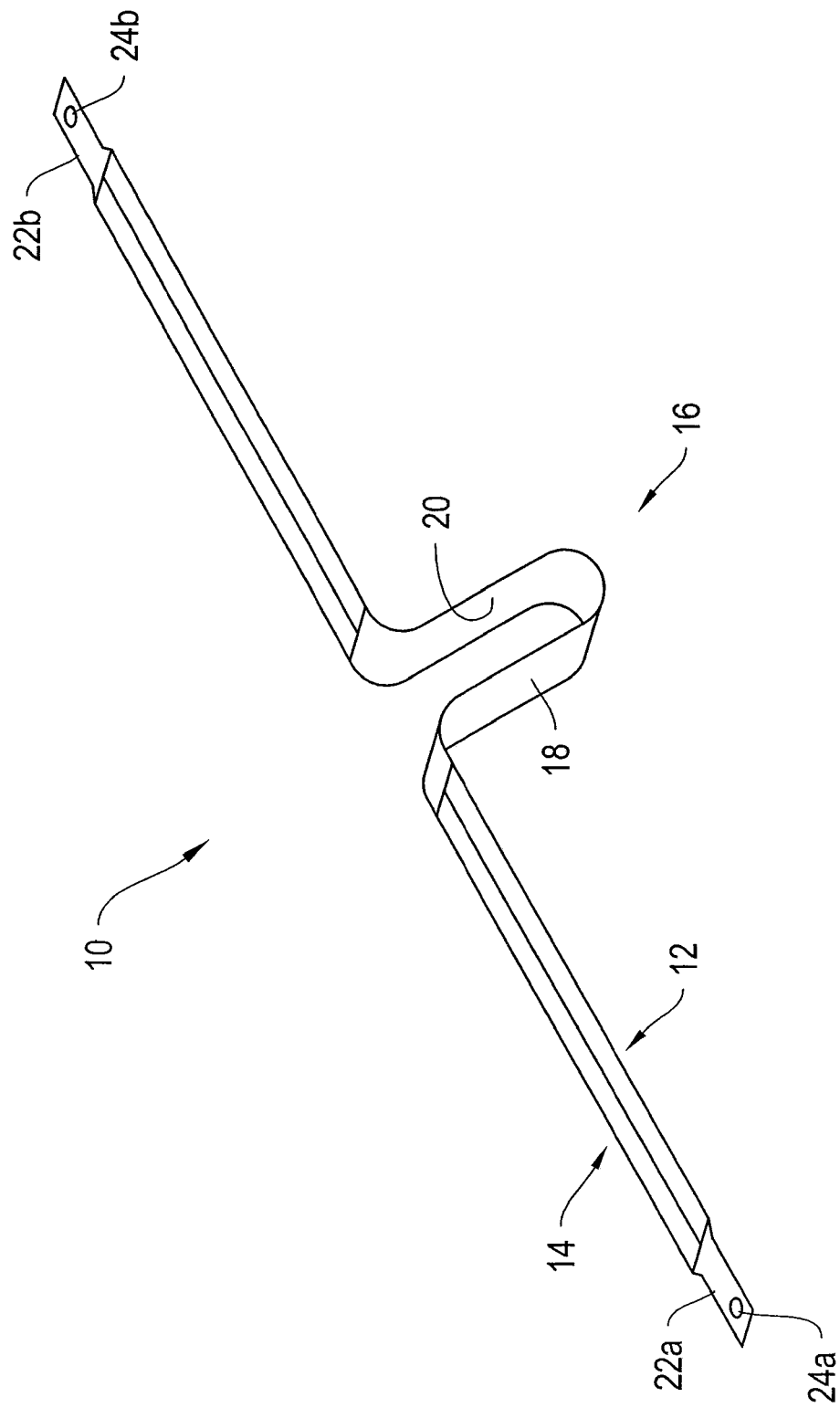
FIG. 1C depicts a perspective top view of a sleeve similar to the sleeve of FIG. 1A, but configured to include a center tab formed from a looped intermediate section of the sleeve according to an illustrative embodiment of the invention.

FIGS. 1A-1D depict various views of a removable sleeve 10 according to illustrative embodiments of the invention. Referring to FIGS. 1A and 1B, the sleeve 10 includes two tabbed end sections 22a and 22b, two flapped sections 26 and 28 and an intermediate section 20. The intermediate section 20 is located between the two flapped sections 26 and 28. In the illustrative embodiment of FIG. 1A, it is located near the middle of the sleeve 10, but this need not be the case. The sleeve 10 also includes two layers, a bottom layer 12 and a top layer 14. The tabbed end sections 22a and 22b include through apertures 24a and 24b sized and shaped to hook onto a distal end of a delivery device. The flapped section 26 is formed from two transversely extending cuts/discontinuities 30a and 30b and a longitudinally extending cut/discontinuity 30c in the top layer 14. The transversely extending discontinuities 30a and 30b separate the flapped section 26 from the tabbed end section 22a and the intermediate section 20, and interoperate with the longitudinally extending discontinuity 30c to create two flaps 32a and 32b. The flaps 32a and 32b are anchored along the longitudinal edges 38a and 38b, respectively, of the sleeve 10. The flaps 32a and 32b open and close independent of each other, and are typically folded inward when the sleeve 10 is employed to at least partially cover a sling. As shown in FIG. 1B, the flaps 32a and 32b may be opened to assist the removal of the sleeve 10 from an associated sling.

In a similar fashion, the flapped section 28 is formed from two transversely extending cuts/discontinuities 34a and 34b and a longitudinally extending discontinuity 34c. The transversely extending discontinuities 34a and 34b separate the flapped section 28 from the intermediate section 20 and the tabbed end section 22b, respectively, of the sleeve 10 and interoperate with the longitudinally extending discontinuity 34c to divide the flapped section 28 into two flaps 36a and 36b. In a similar fashion to the flaps 32a and 32b, the flaps 36a and 36b are anchored along the longitudinal edges 38a and 38b, respectively, of the sleeve 10. The flaps 36a and 36b open and close independent of each other, and are typically folded inward when the sleeve 10 is employed to at least partially cover a sling, and may be opened to assist the removal of the sleeve 10 from the enclosed sling.

Although the sleeve 10 is depicted with the top layer 14 including an intermediate section 20 and tabbed end sections 22a and 22b, this need not be the case. In alternative embodiments, as shown in the sleeve 123 of FIG. 6 below, the intermediate section 20 only has the bottom layer 12, thus eliminating the need for the transversely extending cuts 30a, 30b, 34a and 34b.

According to the illustrative embodiment of FIG. 1A, the longitudinally extending discontinuities 30c and 34c are located substantially in the middle of the flapped sections 26 and 28, respectively, thus dividing each of the flapped sections 26 and 28 into two substantially equally sized flaps. However, this need not be the case. In various other illustrative embodiments, the longitudinally extending discontinuities 30c and 34c may lie anywhere between the first and the second longitudinal edges 38a and 38b of the sleeve 10. In one illustrative embodiment, the longitudinally extending discontinuities 30c and 34c are located along one of the longitudinal edges 38a and 38b, thus creating a single flap for each of the flapped sections 26 and 28. ill another illustrative embodiment, the longitudinally extending discontinuities 30c and 34c are not located in the middle of the flapped sections 26 and 28 or along the longitudinal edges 38a and 38b, thus dividing each of the flapped sections 26 and 28 into two flaps of unequal sizes. According to the illustrative embodiment of FIGS. 1A and 1B, the longitudinally extending discontinuity 30c is located along the same longitudinal axis as the longitudinally extending discontinuity 34c, thus resulting in flapped sections 26 and 28 that are symmetrical relative to each other. However, the longitudinally extending discontinuities 30c and 34c may be located along two different longitudinal axes, resulting in flapped section 26 and 28 that are non-symmetrical relative to each other.

In the illustrative embodiment of FIGS. 1A and 1B, the longitudinally extending discontinuities 30c and 34c are created by longitudinal cuts in the top layer 14 of the sleeve 10. Alternatively, the longitudinally extending discontinuities 30c and 34c may be partial discontinuities through the top layer 14 of the sleeve 10. According to one particular embodiment, such partial discontinuities include perforations, which can be torn, for example, by pulling on the looped portion 16 (shown in FIG. 1C) of the sleeve 10, subsequent to sling assembly placement in the patient's body.

The longitudinally extending discontinuities 30c and 34c may be substantially straight as shown in FIGS. 1A-D. Alternatively, the longitudinally extending discontinuities 30c and 34c may be variously shaped so long as they generally extend along the length of the sleeve 10. By way of example and not intended to be limiting, the discontinuities 30c and 34c may have an angled, wave-like, scalloped, fan-like or zig-zag shape.

Figure 3A:
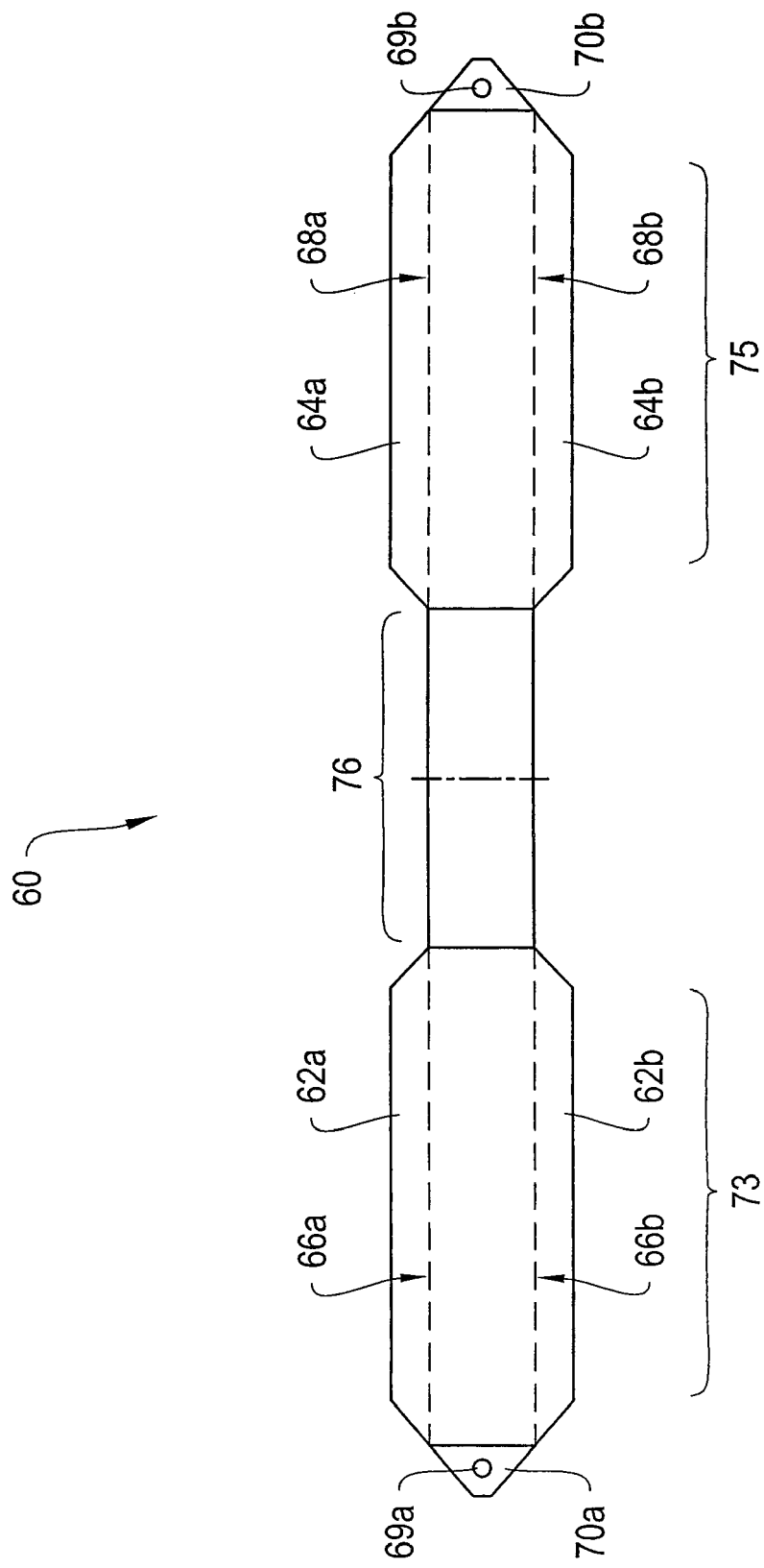
FIG. 3A depicts a top view of a removable sleeve according to another illustrative embodiment of the invention.

The transversely extending discontinuities 30a, 30b, 34a and 34b may also adopt any suitable shapes. In an illustrative embodiment shown in FIG. 1A, all of the transversely extending discontinuities 30a, 30b, 34a and 34b are substantially straight. In an alternative embodiment, one or more of the transversely extending discontinuities 30a, 30b, 34a and 34b are tapered, as shown in FIG. 3A at 64a, FIG. 4A at 64a and FIG. 5 at 108b and 110a.

The flapped sections 26 and 28 may also include additional transversely extending cuts/discontinuities between the sleeve edge 38a and 38b, or between the sleeve edges 38a and 38b and/or the longitudinally extending cut/discontinuity 30c and/or 34c, to further divide the flaps 32a, 32b, 36a and 36b into narrower sub-flaps, each of which being anchored along a longitudinal edge 38a or 38b of the sleeve 10.

According to one illustrative construction, the sleeve 10 is formed from a flattened tube. The edges/creases 38a and 38b of the flat tube provides a hinge about which the flaps 32a, 32b, 36a and 36b open and close. According to the illustrative embodiment, in a closed position, the flaps 32a, 32b, 36a and 36b lay substantially flat.

To facilitate sling delivery, the sleeve 10 may include a center tab 16. As shown in the illustrative embodiment of FIGS. 1C and 1D, the center tab 16 includes a looped middle section 18 of the bottom layer 12 and a looped middle section 20 of the top layer 14. As shown in the cross-sectional view of FIG. 1D, with the middle sections 18 and 20 of the sleeve 10 gathered to form the center tab 16, a gap 44 for exposing a middle section of a covered sling remains. The gap 44, for example, may be between about 0.5 cm and about 10 cm. In other embodiments, it is about 1 cm, about 2 cm, about 3 cm, about 4 cm, about 5 cm, about 6 cm, about 7 cm, about 8 cm, or about 9 cm. The middle sections 18 and 20 of the sling 10 may be secured to form the center tab 16 by any suitable mechanism. According to one illustrative embodiment, the center tab 16 is formed by placing a heat seal just underneath the openings 30b and 34a. In another illustrative embodiment, shown in FIG. 4B, the center tab 86 includes a clip 84 for holding the middle section 76 of the sleeve 60 together. Examples of other embodiments of center tabs are disclosed in commonly assigned U.S. application Ser. No. 10/641,376, the entire contents of which are incorporated herein by reference.

Figure 2:
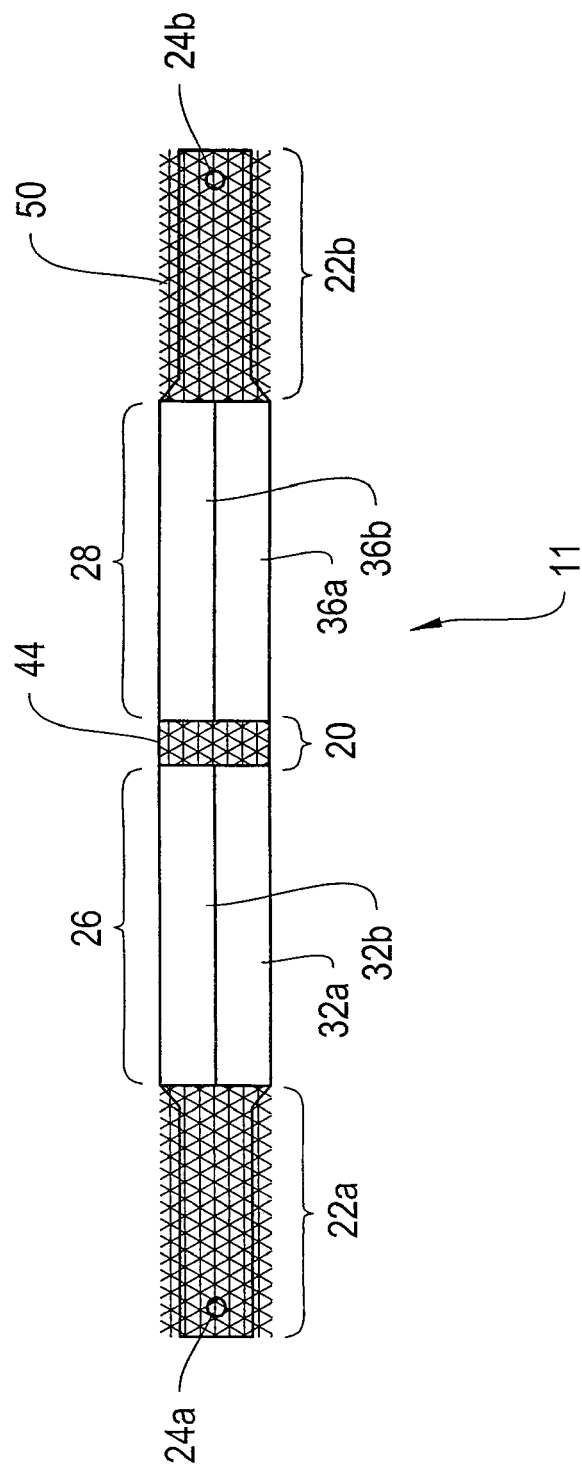
FIG. 2 depicts a sling assembly including a sleeve of the type depicted in FIGS. 1A-1D partially covering a sling.

FIG. 2 shows a top view of a sling assembly 11 including an implantable supportive mesh sling 50 partially covered by the sleeve 10. As configured in FIG. 2, the sling 50 is located on top of the bottom layer 12 in the flapped sections 26 and 28, and on top of the top 14 and the bottom 12 layers in the tabbed end sections 22a and 22b and the intermediate section 20. This configuration exposes the sling 50 along the tabbed end sections 22a and 22b and the intermediate section 20 of the sleeve 10. With the flaps 32a, 32b, 36a and 36b closed, the sling 50 is essentially sandwiched between the top layer 14 and the bottom layer 12 of the sleeve 10 along the flapped sections 26 and 28. Although the sling 50 is depicted as being a mesh sling, any suitable implantable sling may be employed. Preferably the sleeve 10 is formed from a flexible polymer plastic and independent from the sleeve 10. However, any suitable sleeve material may be employed. According to the illustrative embodiment, the sling 50 does not attach to the sleeve 10, but is instead freely moveable and independent from the sleeve. However, in alternative embodiments, the sling 50 may attach to the sleeve 10 at one or more locations.

Figure 1D:
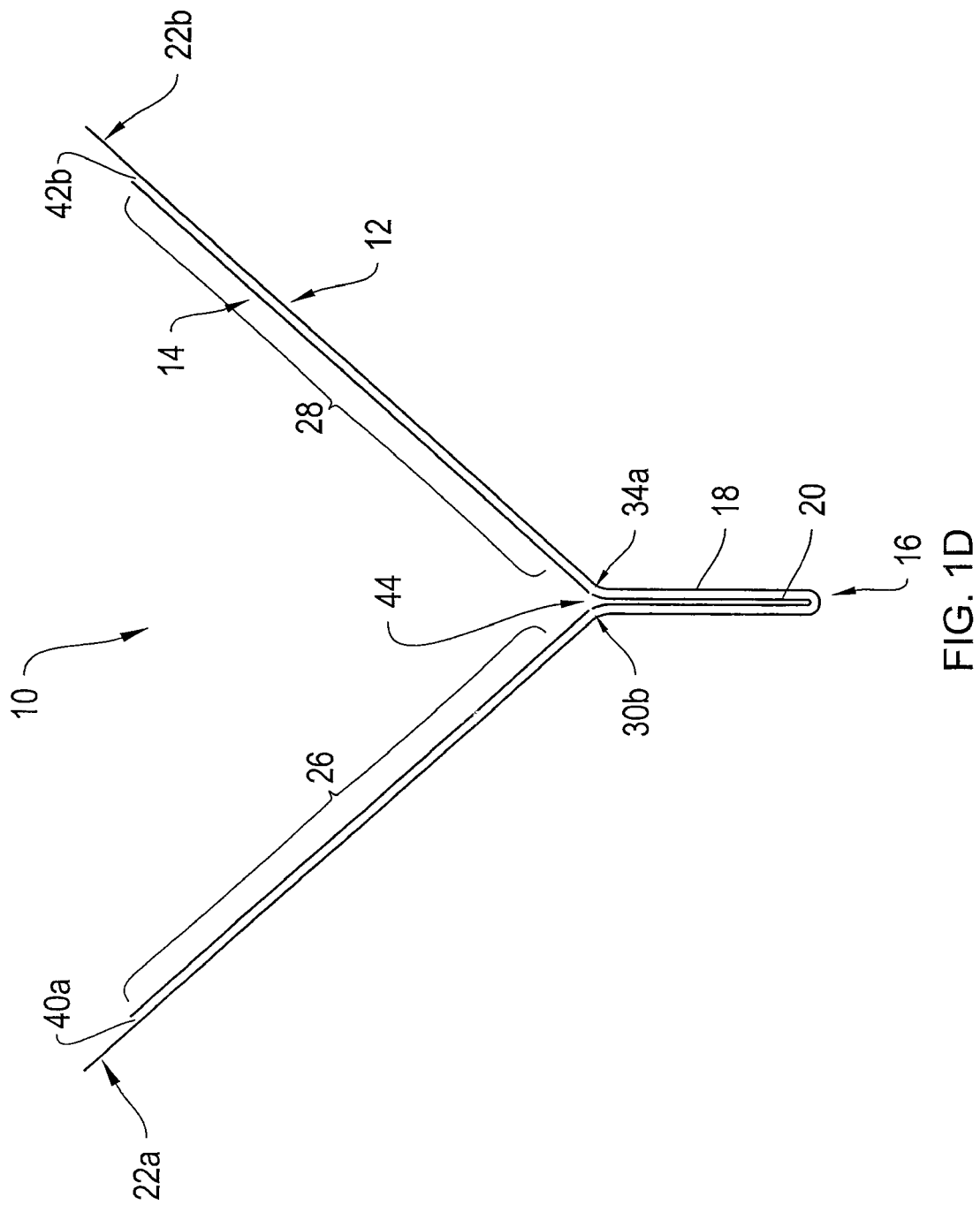
FIG. 1D is a side cross-sectional view of the sleeve of FIG. 1C.

In the illustrative embodiment of FIG. 2, the sling 50 has a length of about 10 cm to about 45 cm and a width of about 1 cm to about 3 cm, though the length and width of the sling can be adapted to the body part of the patient that requires support. By way of example, in some embodiments, the sling is about 45 cm in length and about 1.5 cm in width. The sling may be rectangular, as illustrated in FIG. 2, or have another suitable shape. The sling may have a uniform thickness over the entire length and/or width of sling, or the thickness may vary at one or more locations. According to the illustrative embodiment, the thickness of the sling material ranges from about 2 mm to about 0.10 cm. Additionally, the walls of the sleeve 10 are between about 1 mm to about 0.005 mm thick or about 0.039 inches to about 0.002 inches thick. The flapped sections 26 and 28 have a length of between about one-third and about one-fourth of the length of the sleeve 10. The illustrative flapped sections 26 and 28 are between about 15 cm long and each flap 32a, 32b, 36a and 36b is about 1.5 cm wide. The middle gap 44 is shown as it would be with the center tab 16 formed as shown in FIG. 1D. According to the illustrative embodiment of FIG. 2, the sling 50 is a strip of mesh with any of a number and/or configurations of knits, weaves, or braids, and is sized and shaped for placement in the periurethral tissues of a patient to provide a urethral platform to treat urinary incontinence.

In the illustrative embodiment of FIG. 2, the sleeve 10 and the sling 50 are depicted as being approximately the same length. However, this need not be the case, with the sling 50 being longer or shorter than the sleeve 10 in various other illustrative embodiments. The illustrative flapped sections 26 and 28 are between about 15 cm long and each flap 32a, 32b, 36a and 36b is about 1.5 cm wide. The middle gap 44 is shown as it would be with the center tab 16 formed as shown in FIG. 1D.

As depicted, the sling 50 does not include any apertures particularly formed for hooking onto a delivery device. In this configuration, one or more of the mesh openings may be used for such purpose. According to one illustrative embodiment, the mesh openings employed for such a purpose are spaced two or more openings from the sling ends to provide increased structural integrity and to avoid tearing at a mesh end. In other illustrative embodiments, the sling 50 may include particularly formed apertures aligned with the apertures 24a and 24b in the end tabs 22a and 22b, respectively, for hooking onto a delivery device. In this configuration, it is also advantageous to space the apertures between about 0.25 cm and about 1 cm from the ends of the sling 50.

FIGS. 3A and 3B depicts a sleeve 60 according to an alternative embodiment of the invention. Referring to the top view of the sleeve 60 shown in FIG. 3A, it includes two tabbed end sections 70a and 70b, two flapped sections 73 and 75, and a middle section 76. The sleeve 60 is formed from a single layer, and may, for example, be made from a single flat sheet of material. The two tabbed end sections 70a and 70b include through apertures 69a and 69b sized and shaped to hook onto a distal end of a delivery device. The flapped sections 73 and 75 are formed by folding the single layer 79 of the flat sheet material along the dotted lines 66a, 66b, 68a and 68b, forming four flaps 62a, 62b, 64a and 64b, respectively. Each flap 62a, 62b, 64a and 64b opens and closes independent of each other, and is typically folded inward to form a partial top layer 71 to at least partially covering a sling. The flaps 62a, 62b, 64a and 64b open to assist the removal of the sleeve 60 from an associated sling. The width of the flaps 62a, 62b, 64a and 64b may vary. In one illustrative embodiment, shown in FIG. 4A, when the flaps 62a, 62b, 64a and 64b are closed, neither flap pair 62a and 62b, nor flap pair 64a and 64b abut each other. Instead, gap 78 extends longitudinally between them, exposing longitudinally an extending intermediate portion of the sling 80. In an alternative embodiment, when the flaps 62a, 62b, 64a and 64b are closed, the flap 62a may abut or overlap with the flap 62b, and the flap 64a may abut or overlap with the flap 64b and thus leaving no longitudinally extending gap. The shapes of the flaps 62a, 62b, 64a and 64b may also vary. In the illustrative embodiment of FIG. 3A, each of the flaps 62a, 62b, 64a and 64b and the end tabs 70a and 70b have tapered ends for easy insertion and removal of the sleeve 60 from a sling that it at least partially covers. However, this need not be the case. The flaps 62a, 62b, 64a and 64b and the end tabs 70a and 70b may adopt any suitable shapes as described above with respect to FIGS. 1A-1D. The longitudinally and transversely extending edges of the flaps 62a, 62b, 64a and 64b and the end tabs 70a and 70b may be of any suitable shape, including without limitation straight, tapered, or may be wavy, scalloped, fan-shaped, rounded or zig-zag shaped. As shown in FIG. 3A, the flaps 62a, 62b, 64a and 64b are of identical shapes and sizes. However, this need not be the case. In various other illustrative embodiments, the flaps 62a, 62b, 64a and 64b are of different shapes and sizes from each other.

In a similar fashion to the sleeve 10, to facilitate sling delivery, the sleeve 60 may include a center tab 77. As shown in the illustrative embodiment of FIG. 3B, the center tab 77 includes a looped middle section 76 of the sleeve 60. With the middle section 76 of the sleeve 60 gathered to form the center tab 77, a gap 72 for exposing a middle section of a covered sling remains. The gap 72, for example, may be between about 0.5 cm and about 10 cm. In other embodiments, it is about 1 cm, about 2 cm, about 3 cm, about 4 cm, about 5 cm, about 6 cm, about 7 cm, about 8 cm, or about 9 cm. The middle section 76 of the sling 60 may be secured to form the center tab 77 by any suitable mechanism. According to one illustrative embodiment, the center tab 77 is formed by placing a heat seal just underneath the gap 72. In another illustrative embodiment, shown in FIG. 4B, the center tab includes a clip for holding the middle section 76 of the sleeve 60 together. As shown in FIG. 3B, the sleeve 60 includes a bottom layer 79 and at least a partial top layer 71, which is formed when the flaps 62a, 62b, 64a and 64b are closed.

Figure 4A:
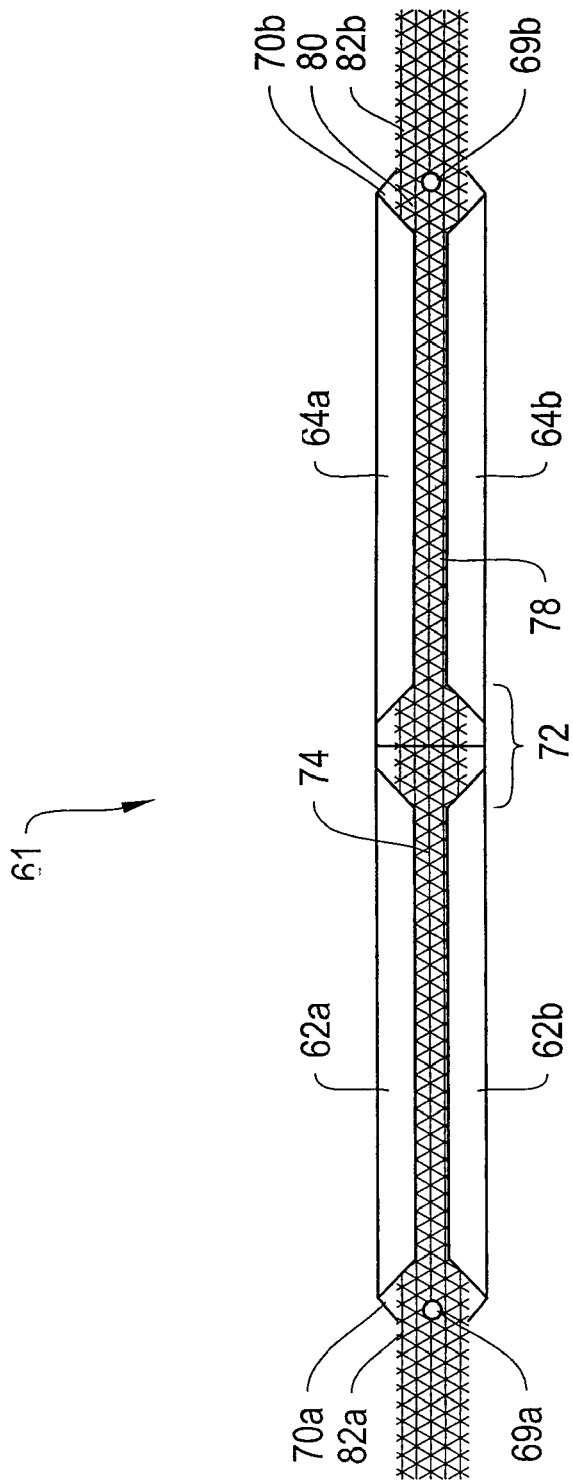
FIG. 4A depicts a top view of a sling assembly including a removable sleeve of the type depicted in FIGS. 3A and 3B partially covering a sling.

FIG. 4A and FIG. 4B depict a top view and a side view, respectively, of a sling assembly 61 including an implantable supportive mesh sling 80 partially covered by the sleeve 60. According to this illustrative embodiment, the sling 80 is longer than the sleeve 60, with the ends 82a and 82b of the sling 80 overhanging the sleeve 60. As shown, the sling 80 is located on top of bottom layer 79 of the sleeve 60. The flaps 62a, 62b, 64a and 64b fold over to partially sandwich the sling 80 between the flaps 62a, 62b, 64a and 64b and the bottom layer 79 of the sleeve 60. A gap 72, located between the flap pairs 62a, 62b and 64a and 64b, exposes the entire width of a middle section of the sling 80. The sling 80 is additionally exposed along the tabbed end sections 70a and 70b.

FIG. 4B also shows an alternative approach to forming a center tab 86. Instead of the heat seal of FIG. 1D, a clip 84 holds the looped middle section 76 of the sleeve 60 together to form the center tab 86. This embodiment may be used in connection with any of the sleeves of the invention, including, the protective sleeve 10 shown in FIGS. 1A-1D and the protective sleeve 60 shown in FIGS. 3A and 3B. According to the illustrative embodiment, the clip 84 also captures a looped portion 92 of the sling 80. A medical operator may adjust the length of the loop portion 92 of the sling 80 prior to its placement to adjust the length and/or tensioning of the sling 80. Illustratively, to prevent over tensioning of a sling, a medical operator places a hemostat, a scissors or other type of spacer between the urethra and the sling during the sling placement to ensure ample looseness of the sling. The looped portion 92 of the sling 80 eliminates the need for a spacer during placement. The looped portion 92 should generally equal to the length of the mesh sling that would have been provided by a spacer.

Figure 5:
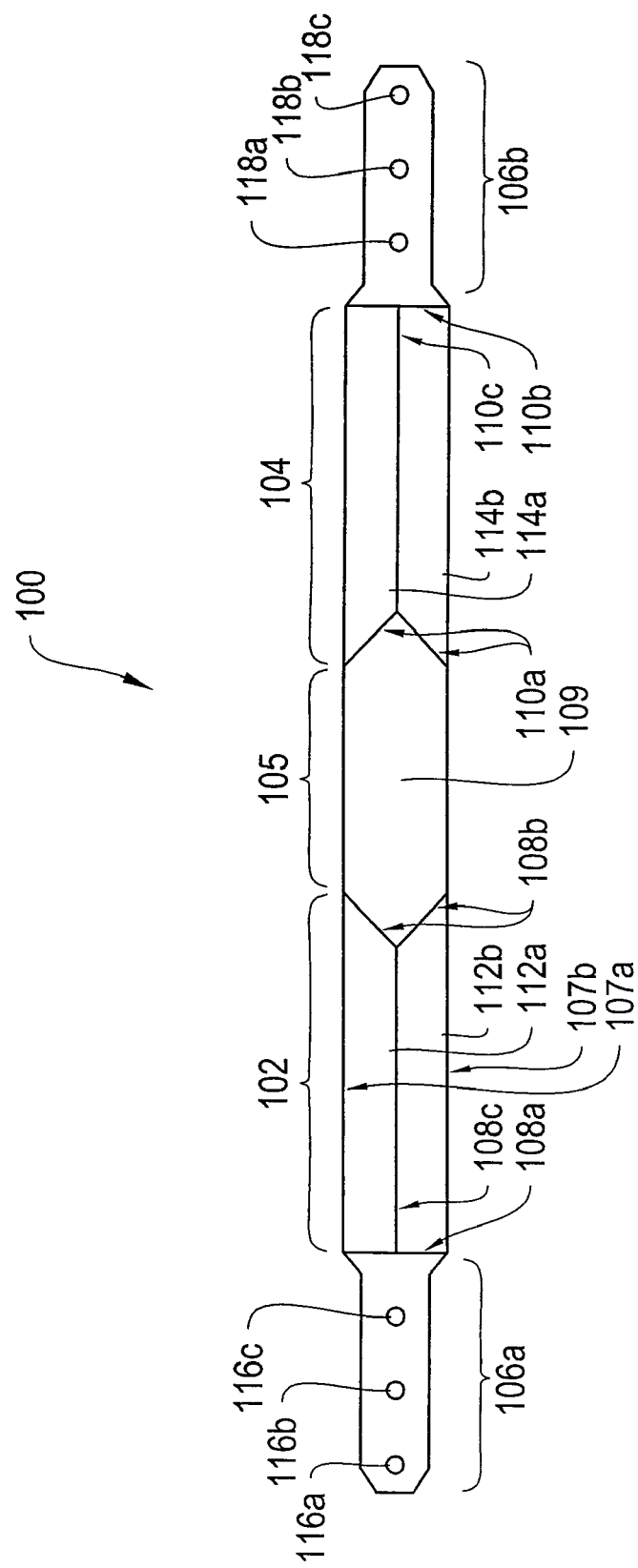
FIG. 5 depicts a top view of a removable sleeve having a similar configuration to the sleeve of FIG. 1A and including three through apertures on each tabbed end section according to another alternative embodiment of the invention.

FIG. 5 depicts a top view of a removable sleeve 100 according to another illustrative embodiment of the invention. The sleeve 100 includes two layers, a top layer 101 and a bottom layer 103. The top layer 101 of the sleeve 100 includes two flapped sections 102 and 104, and a gap 105 in the middle between the flapped sections 102 and 104, exposing the middle section 109 of the bottom layer 103 of the sleeve 100. The flapped section 102 is formed from two transversely extending discontinuities 108a and 108b and a longitudinally extending cut/discontinuity 108c in the top layer 101. The transversely extending discontinuities 108a and 108b interoperate with the longitudinally extending cut/discontinuity 108c to create two flaps 112a and 112b. The flaps 112a and 112b are anchored along the longitudinal edges 107a and 107b, respectively, of the sleeve 100. The flaps 112a and 112b open and close independent of each other, and are typically folded inward when the sleeve 100 is employed to at least partially cover a sling. The flaps 112a and 112b may be opened to assist the removal of the sleeve 100 from an associated sling.

In a similar fashion, the flapped section 104 is formed from two transversely extending discontinuities 110a and 110b and a longitudinally extending cut/discontinuity 110c in the top layer 101. The transversely extending discontinuities 110a and 110b interoperate with the longitudinally extending discontinuity 110c to create two flaps 114a and 114b. The flaps 114a and 114b are anchored along the longitudinal edges 107a and 107b, respectively, of the sleeve 100. The flaps 114a and 114b open and close independent of each other, and are typically folded inward when the sleeve 100 is employed to at least partially cover a sling. The flaps 114a and 114b may be opened to assist the removal of the sleeve 100 from an associated sling.

The bottom layer 103 of the sleeve 100 includes two tabbed end sections 106a and 106b. Each of the tabbed end sections 106a and 106b includes three through apertures 116a, 116b, 116c, and 118a, 118b and 118c, respectively, which through apertures are sized and shaped to hook onto a distal end of a delivery device. The three through apertures allow for adjustment of the length of a sling, such as the sling 80. If a longer sling is desired, a delivery device can be inserted into the through apertures 116a and 118c of the sleeve 100 and through a corresponding aperture or a corresponding mesh opening in the sling at least partially covered by the sleeve 100. Alternatively, if a shorter sling is desired, a delivery device can be inserted into the through apertures 116c and 118a of the sleeve 100 and through a corresponding aperture or a corresponding mesh opening in the sling at least partially covered by the sleeve 100 and the excess sling and sleeve 100 can be trimmed off before sling placement, thus shortening the sling length. The through apertures 116a, 116b, 116c, and 118a, 118b and 118c may be, for example, 0.25 cm and 2 cm apart. In other embodiments, they are about 0.5 cm, about 1 cm or about 1.5 cm apart. In an alternative illustrative embodiment, the excess sling and sleeve can be left overhanging the delivery device and inserted into the body. In certain other illustrative embodiments, the tabbed end sections 106 and 106b of the sleeve 100 may each have two through apertures or have more than three through apertures.

The sleeve 100 is depicted with the middle section 109 and the two tabbed end sections 106 and 106b having only the bottom layer 103, thus the discontinuities 108a, 108b, 110a and 110b are just the ends of the top layer 101, not cuts. In alternative embodiments, the top layer 101 of the sleeve 100 includes a middle section and two tabbed end sections, thus necessitates the need for transverse cuts in the top layer 101 that create the transverse discontinuities 108a, 108b, 110a and 110b.

According to the illustrative embodiment of FIG. 5, the longitudinally extending discontinuities 108c and 110c are located substantially in the middle of the flapped sections 102 and 104, respectively, thus dividing each of the flapped sections 102 and 104 into two substantially equally sized flaps. However, this need not be the case. In various other illustrative embodiments, the longitudinally extending discontinuities 108c and 110c may lie anywhere between the first and the second longitudinal edges 107a and 107b of the sleeve 100. In one alternative embodiment, the longitudinally extending discontinuities 108c and 110c are located along one of the longitudinal edges 107a and 107b, thus creating a single flap for each of the flapped sections 102 and 104. In another illustrative embodiment, the longitudinally extending discontinuities 108c and 110c are not located in the middle of the flapped sections 102 and 104, thus dividing each of the flapped sections 102 and 104 into two flaps of unequal size. According to the illustrative embodiment of FIG. 5, the longitudinally extending discontinuity 108c is located along the same longitudinal axis as the longitudinally extending discontinuity 110c, thus resulting in flapped sections 102 and 104 that are symmetrical relative to each other. However, the longitudinally extending discontinuities 108c and 110c may be located along two different longitudinal axes, resulting in flapped section 102 and 104 that are non-symmetrical relative to each other.

In the illustrative embodiment of FIG. 5, the longitudinally extending discontinuities 108c and 110c are created by longitudinal cuts in the top layer 101 of the sleeve 100. Alternatively, the longitudinally extending discontinuities 108c and 110c may be partial discontinuities through the top layer 101 of the sleeve 100. According to one embodiment, such partial discontinuities include perforations, which may be torn, for example, by pulling on a looped portion formed from the middle section 109 of the sleeve 100, subsequent to sling assembly placement.

The longitudinally extending discontinuities 108c and 110c may be substantially straight as shown in FIG. 5. Alternatively, the longitudinally extending discontinuities 108c and 110c may be variously shaped so long as they generally extend along the length of the sleeve 100. By way of example and not intended to be limiting, the discontinuities 108c and 110c may have an angled, wave-like, scalloped, fan-like or zig-zag shape.

The transversely extending discontinuities 108a, 108b, 110a and 110b may also adopt any suitable shapes. In the illustrative embodiment of FIG. 5, the transversely extending discontinuities 108a and 110b are substantially straight, while the transversely extending discontinuities 108b and 110a are tapered in shape. The flapped sections 102 and 104 may also include additional transversely extending cuts/discontinuities between the sleeve edge 107a and/or 107b and the longitudinally extending cut/discontinuity 108c and/or 110c, or extending between the sleeve edges 107a and 107b, to further divide the flaps 112a, 112b, 114a and 114b into narrower sub-flaps, each of which being anchored along a longitudinal edge 107a and 107b of the sleeve 100.

According to one illustrative embodiment, the sleeve 100 is formed from a flattened tube. The edges/creases 107a and 107b of the flat tube provide a hinge about which the flaps 112a, 112b, 114a and 114b open and close. In a closed position, the flaps 112a, 112b, 114a and 114b lay substantially flat.

Figure 6:
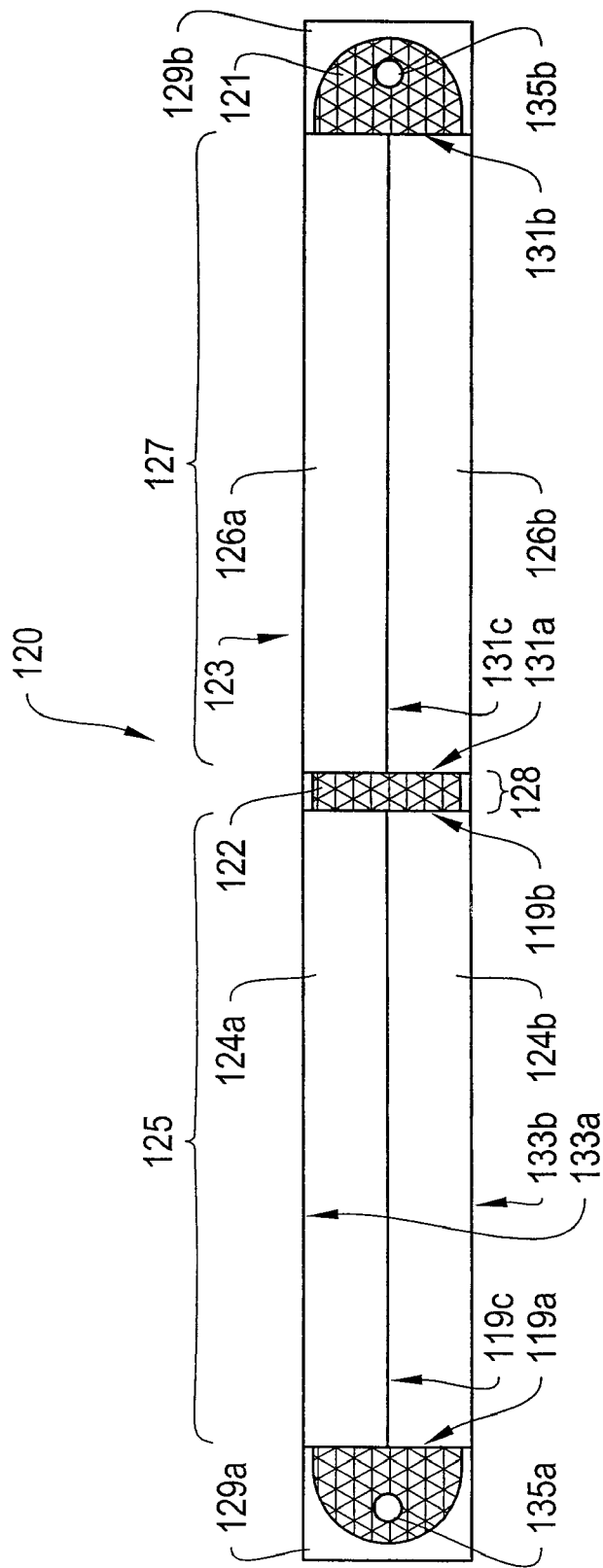
FIG. 6 depicts a top view of a sling assembly including a sleeve partially covering a sling according to an alternative embodiment of the invention.

FIG. 6 shows a top view of a sling assembly 120 including an implantable supportive mesh sling 121 partially covered by the sleeve 123 according to another illustrative embodiment of the invention. The sleeve 123 is configured similarly to the sleeve 10 shown in FIGS. 1A-1D. The sleeve 123 includes two layers, a top layer and a bottom layer. The top layer of the sleeve 123 includes two flapped sections 125 and 127 and a gap 122, between the two flapped sections 125 and 127, which corresponds to the middle section 128 of the bottom layer of the sleeve 123. The bottom layer of the sleeve 123 includes a middle section 128 and two tabbed end sections 129a and 129b, each of which includes a through aperture 135a and 135b, respectively sized and shaped to hook onto a distal end of a delivery device. The flapped section 125 is formed from two transversely extending discontinuities 119a and 119b and a longitudinally extending cut/discontinuity 119c in the top layer of the sleeve 123. The transversely extending discontinuities 119a and 119b interoperate with the longitudinally extending discontinuity 119c to create two flaps 124a and 124b. The flaps 124a and 124b are anchored along the longitudinal edges 133a and 133b, respectively, of the sleeve 123. The flaps 124a and 124b open and close independent of each other, and are typically folded inward when the sleeve 123 is employed to at least partially cover a sling. The flaps 124a and 124b may be opened to assist the removal of the sleeve 123 from an associated sling.

In a similar fashion to the flapped section 125, the flapped section 127 is formed from two transversely extending discontinuities 131a and 131b and a longitudinally extending cut/discontinuity 131c. The transversely extending discontinuities 131a and 131b interoperate with the longitudinally extending discontinuity 131c to divide the flapped section 127 into two flaps 126a and 126b. As in the case of the flaps 124a and 124b, the flaps 126a and 126b are anchored along the longitudinal edges 133a and 133b, respectively, of the sleeve 123. The flaps 126a and 126b open and close independent of each other, and are folded inward when the sleeve 123 is employed to at least partially cover a sling. They may be opened to facilitate removal of the sleeve 123 from the enclosed sling 121. As configured in FIG. 6, the sling 121 is located on top of the bottom layer of the sleeve 123. With the flaps 124a, 124b, 126a and 126b closed, the sling 121 is essentially sandwiched between the top layer and the bottom layer of the sleeve 123 along the flapped sections 125 and 127 and is exposed along the tabbed end sections 129a and 129b and the gap 122. According to this illustrative embodiment, the tangs of the sling 121 are covered in the protective sleeve 123. The exposed portions of the sling 121 are non-tanged. The sling assembly 120 of this illustrative embodiment may be useful for delivering the sling, for example, 121 through an incision or incisions besides the vaginal incisions.

The sleeve of the invention may be made, for example, from one or more absorbent materials, such as a sponge-like material, which can optionally be pre-soaked in a drug solution, for example, in an anesthetic, anti-inflammatory, coagulating, anticoagulating, or antibiotic solution. In a preferred embodiment, the sleeve may be made from bio-compatible and flexible material. In another embodiment, the sleeve may be made from a non-wettable material, such as polypropylene, polyethylene, polyester, polytetrafluoroethylene (available from DuPont Corporation, Wilmington, Del., under the trademark TEFLON®), TYVEK®, MYLAR®, or co-polymers thereof. The non-wettable materials may also be pre-treated with a therapeutically effective drug coating. The material of the sleeve may be a single layer or consist of multiple layers. The sleeve, preferably, is transparent so that an operator will be able to see the implantable sling inside the sleeve. The sleeve may be made of or include bioabsorbable materials. Examples of bioabsorbable sleeves, and examples of materials for making such sleeves, are disclosed in commonly assigned U.S. patent application Ser. No. 10/631,364, the contents of which are incorporated herein by reference in their entirety.

The sling used with the invention may be fabricated from any of a number of biocompatible materials, such as nylon, polyethylene, polyester, polypropylene, fluoropolymers, copolymers thereof, combinations thereof, or other suitable synthetic material(s). The material may be, for example, a synthetic material that is absorbable by the patient's body. Suitable absorbable synthetic materials can include polyglycolic acid, polylactic acid, and other suitable absorbable synthetic materials. Alternatively, the material for the sling may be derived from mammalian tissue(s) or a combination of mammalian tissue(s) and synthetic material (s). The sling material may be fabricated from one or more yarns, which yarns may be made from one or more materials. The sling may incorporate or be coated with one or more agents to provide a therapeutic effect, for example, to reduce discomfort, to reduce the chance of infection and/or to promote tissue growth.

The edge regions of the sling used with the invention can be configured differently depending on their intended placement in the body of the patient. For example, a middle section of the sling is typically located where an anatomical site, such as a midurethral or bladder neck location in the periurethral tissue, needs to be supported. In one illustrative embodiment, the middle section of the sling has smooth or rounded edges, hereinafter also referred to as "non-tanged." According to a further illustrative embodiment, other sections of the sling may include tangs (e.g., sharp projections or frayed edges). The tangs are generally useful for anchoring the sling and encouraging tissue growth into the sling. Anchoring the sling in this manner generally obviates the need for additional sutures to hold the sling in place. Anchoring the sling via its tangs is especially useful for anchoring the sling on a tissue and facilitating the removal of the sleeve according to the invention by pulling on the center tab of the sleeve while the sling stays in place, without the need for additional incisions in order to hold the sling external to the body while the sleeve is being removed through pulling.

The tanged and non-tanged edges of the sling may be formed in a plurality of ways. For example, the sling can be cut from a woven sheet, in which case the edges would be initially tanged along the entire length of the sling. One or more non-tanged sections may be formed by any process that smoothes, rounds or removes the sharp edges of the tangs. For example, the tangs may be heat-smoothed by burning or melting the tangs. In one embodiment, the non-tanged section has a length of about 1 cm to about 5 cm, preferably about 2 cm to about 2.5 cm, on either or both sides of the center of the sling. Providing one or more non-tanged sections, which may be in. close proximity to a sensitive anatomical site in the patient, can enhance the comfort level of the patient and reduce the potential for the edges of the tangs to erode or irritate the urethra. Alternatively, the sling can be produced from a woven tape having the approximate finished width of the sling. The smooth sides of the tape can then be trimmed off to produce the tanged sections.

Figure 7:
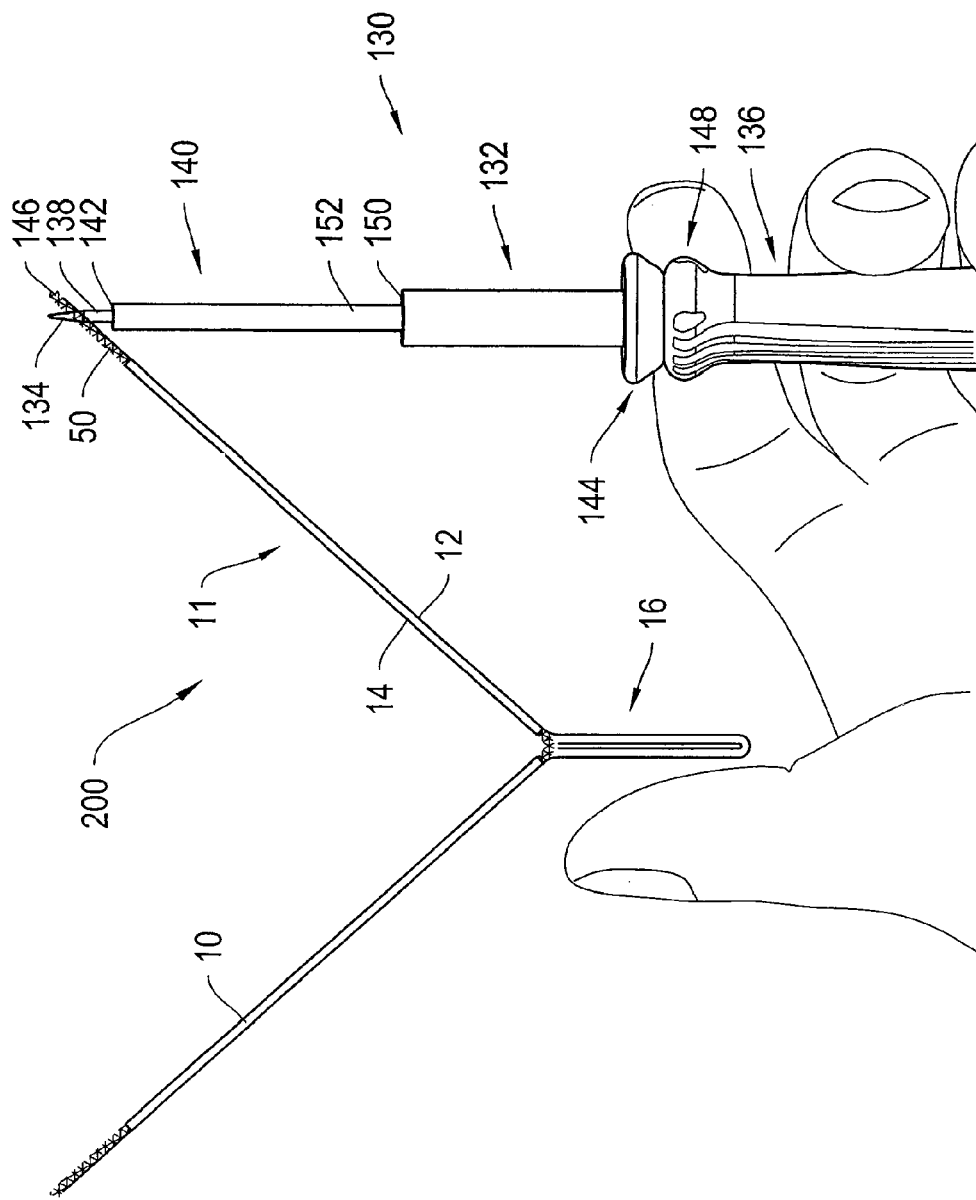
FIG. 7 schematically depicts a sling delivery system including a delivery device and a sling assembly according to an illustrative embodiment of the invention.

FIG. 7 depicts an illustrative sling delivery system 200 for delivering a mesh sling 50 through a single incision such as, for example, a midline incision in a vaginal wall, according to an illustrative embodiment of the invention. As shown in FIG. 7, the sling delivery system 200 includes a delivery device 130, which is assembled with the sling assembly 11. The sling assembly 11 includes the sleeve 10 and the sling 50, as depicted in FIG. 2. The delivery device 130 includes a handle 136 and a shaft 138 extending distally from the handle 136. The shaft 138 includes a distal tip 134 for slidably interfitting with the sling end 146 of the sling 50. The delivery device 130 also includes a pusher assembly 140, which slidably interfits over the shaft 138 and abuts the distal end 148 of the handle 136.

The distal end tip 134 of the delivery device 130 slides through a through aperture 24a of the sleeve 10 and through a mesh opening (or a through aperture) in the sling 50 until the sling 50 and the sleeve 10 rest on the shoulder 142 of the pusher assembly 140. A distal end of the pusher assembly 140 forms a radially outwardly extending shoulder 142 around the circumference of the shaft 138 and functions to impede the sling end 146 from sliding proximally along a substantial portion of the length of the shaft 138. The sling assembly 11 is oriented such that the top layer 14 of the sleeve 10 faces the urethra. A medical operator may use a thumb to hold the center tab 16 of the sling assembly 11 against the handle 136 of the delivery device 130 to maintain the sling assembly 11 hooked onto the delivery device 130 during insertion. The center tab 16 can be used as a visual aid to the placement of the sling assembly 11. For example, after a midline incision is made, the sling assembly 11 is first advanced and directed through the midline incision on the right side of the patient until the center tab 16 of the sling assembly 11 is about underneath the urethra. Once the first end of the sling assembly 11 is placed at a desired anatomical location, the medical operator pushes the actuator 144 of the pusher assembly 130 in a distal direction, causing the shoulder 142 to push the sling end 146 distally off the distal tip 134 of the shaft 138. Next, the same or a different delivery device 130 is inserted through the through aperture 24b of the sleeve 10 and through a mesh opening (or a through aperture) in the sling 50 and the same procedure described above is repeated to deliver the sling assembly 11 on the left side of the patient. The sling ends may be delivered to any suitable location within the patient's body.

After the sling assembly 11 is positioned within the patient, the medical operator can simply pull the center tab 16 outward away from the incision. The non-sleeved, exposed tangs of the sling 50 have engaged the tissue on both ends of the sling assembly. By pulling the center tab 16 of the sleeve 10, the flaps 32a, 32b, 36a and 36b on the top layer 14 of the sleeve 10 open while the sling 50 remains stationary. Continually pulling the center tab 16 removes the protective sleeve 10 away from the sling 50. In this way, the sleeve 10 can be removed from the sling 50 from the same orifice through which the insertion of the sling assembly 11 is made, thus eliminating the need for any additional incision, such as an ishipubic incision or an abdominal incision, which is required for sleeve removal for currently available sling assemblies. As described above, the use of the sleeve 10 of the invention also eliminates the need for cutting the center tab 16 in order to remove the sleeve 10 from the sling 50. Although FIG. 7 depicts the delivery of the sling assembly 11 including the sleeve 10, other embodiments of the sleeves, including the sleeve 60 as depicted in FIGS. 3A, 3B, 4A and 4B, the sleeve 100 as depicted in FIG. 5, can be used in the same manner.

Other suitable delivery devices may also be used with the sling assembly of the invention, including, for example, those described in U.S. application Ser. No. 10/973,010 entitled "Systems and Methods Relating to Anchoring a Medical Implant to Tissue" and filed on Oct. 25, 2004, and U.S. application Ser. No. 10/642,395 entitled "Systems, Methods and Devices Relating to Delivery of Medical Implants" and filed on Aug. 14, 2003, the entire contents of which are incorporated herein by reference.

As mentioned above, the sleeve of the invention enables the delivery of a sling assembly and removal of the sleeve through a single incision. The sleeve of the invention may also be used with embodiments in which the sleeve is used to deliver a sling through more than one incisions, including more than one vaginal incision, abdominal incision or ishiopubic incision. The sling may be delivered via abdominal, suprapubic, prepubic, transvaginal, transobturatoral or other approaches.

According to a transvaginal approach, the delivery device is advanced through an incision in the vaginal wall toward an abdominal incision on the right side of a patient until the first end of the sling assembly emerges from the abdominal incision. Then, the delivery device is withdrawn and the second end of the sling assembly is connected to the same or second delivery device, and inserted through the vaginal incision and advanced toward the abdominal incision on the left side of the patient until the second end of the sling assembly emerges from the abdominal incision or the ishiopubic incision.

According to an abdominal approach, the distal end of the delivery device is inserted into an abdominal incision down to a vaginal incision. The distal tip of the shaft then hooks a first end of the sling assembly. The shaft is then pulled back pulling the sling assembly through the path the shaft has created in the body of the patient until the first end of the sling assembly emerges at the abdominal incision. The same procedure is repeated with the second end of the sling assembly, with the same or different delivery device.

According to a transobtural approach, the shaft of the delivery device may be advanced through a vaginal incision toward an ishiopubic incision to deliver each sling end to a respective obturator foramen. Alternatively, the shaft of the delivery device may be advanced through an ishiopubic incision and through an incision in the vaginal wall. A sling assembly end may then be hooked on to the distal end of the shaft. The shaft can then be withdrawn to place each sling end in a respective obturator foramen. In other alternative procedures the sling ends attach to soft tissue anchors, which are left implanted in the patient's body to secure the sling in place.

After the placement of the sling assembly as described above, the sling assembly can be adjusted external to the body (instead of using the center tab to adjust the sling). The sleeve can then be removed via the vaginal incision by pulling on the center tab and opening up the flaps on the sleeve, while the sling ends may be held external to the body (instead of relying on the tangs of the sling to engage the tissue for the sling to remain stationary during the removal of the sleeve). Any embodiments of the sleeves in the application may be used to deliver a sling through more than one incisions as described above. Preferably, to minimize the irritation on the tissue that may be caused by exposed tangs on a sling during the placement procedure, the sling assembly 120 as depicted in FIG. 6, with the tangs of the sling 121 completely enclosed in the sleeve 123, is used for sling delivery through incisions besides the vaginal incision.

The invention described herein may be employed with any suitable sling or sling assembly, any suitable sling delivery device or approach, any suitable sling assembly-to-delivery device association mechanism, and any suitable anchoring mechanism or none at all.

Without limitation, examples slings, sling assemblies, sling delivery devices and approaches, sling assembly-to-delivery device association mechanisms, and sling anchoring mechanisms with which the invention may be employed disclosed in U.S. Pat. No. 6,042,534, entitled "Stabilization sling for use in minimally invasive pelvic surgery," U.S. Pat. No. 6,755,781, entitled "Medical slings," U.S. Pat. No. 6,666,817, entitled "Expandable surgical implants and methods of using them," U.S. Pat. No. 6,042,592, entitled "Thin soft tissue surgical support mesh," U.S. Pat. No. 6,375,662, entitled "Thin soft tissue surgical support mesh," U.S. Pat. No. 6,669,706, entitled "Thin soft tissue surgical support mesh," U.S. Pat. No. 6,752,814, entitled "Devices for minimally invasive pelvic surgery," U.S. Ser. No. 10/918,123, entitled "Surgical Slings," U.S. patent application Ser. No. 10/641,376, entitled "Spacer for sling delivery system," U.S. patent application Ser. No. 10/641,192, entitled "Medical slings," U.S. Ser. No. 10/641,170, entitled "Medical slings," U.S. Ser. No. 10/640,838, entitled "Medical implant," U.S. patent application Ser. No. 10/460,112, entitled "Medical slings," U.S. patent application Ser. No. 10/631,364, entitled "Bioabsorbable casing for surgical sling assembly," U.S. Ser. No. 10/092,872, entitled "Medical slings," U.S. patent application Ser. No. 10/939,191, entitled "Devices for minimally invasive pelvic surgery," U.S. patent application Ser. No. 10/774,842, entitled "Devices for minimally invasive pelvic surgery," U.S. patent application Ser. No. 10/774,826, entitled "Devices for minimally invasive pelvic surgery," U.S. Ser. No. 10/015,114, entitled "Devices for minimally invasive pelvic surgery," U.S. patent application Ser. No. 10/973,010, entitled "Systems and methods for sling delivery and placement," U.S. patent application Ser. No. 10/957,926, entitled "Systems and methods for delivering a medical implant to an anatomical location in a patient," U.S. patent application Ser. No. 10/939,191, entitled "Devices for minimally invasive pelvic surgery," U.S. patent application Ser. No. 10/918,123, entitled "Surgical slings," U.S. patent application Ser. No. 10/832,653, entitled "Systems and methods for sling delivery and placement," U.S. patent application Ser. No. 10/642,397, entitled "Systems, methods and devices relating to delivery of medical implants," U.S. patent application Ser. No. 10/642,395, entitled "Systems, methods and devices relating to delivery of medical implants," U.S. patent application Ser. No. 10/642,365, entitled "Systems, methods and devices relating to delivery of medical implants," U.S. patent application Ser. No. 10/641,487, entitled "Systems, methods and devices relating to delivery of medical implants," U.S. patent application Ser. No. 10/094,352, entitled "System for implanting an implant and method thereof," U.S. patent application Ser. No. 10/093,498, entitled "System for implanting an implant and method thereof," U.S. patent application Ser. No. 10/093,450, entitled "System for implanting an implant and method thereof," U.S. patent application Ser. No. 10/093,424, entitled "System for implanting an implant and method thereof," U.S. patent application Ser. No. 10/093,398, entitled "System for implanting an implant and method thereof," and U.S. patent application Ser. No. 10/093,371, entitled "System for implanting an implant and method thereof," the entire contents of all of which are incorporated herein by reference.

What is claimed is:

1. A sling assembly comprising:
   an implantable sling sized and shaped for providing a urethral platform; and
   a removable sleeve for covering, at least partially, the implantable sling, the removable sleeve including:
      a first flapped portion having a first flap transversely folded over the implantable sling relative to a longitudinal axis of the removable sleeve;
      a second flapped portion having a second flap transversely folded over the implantable sling relative to the longitudinal axis of the removable sleeve; and
      a middle portion disposed between the first flapped portion and the second flapped portion, the middle portion defining a gap between the first flap and the second flap,
   the first flap and the second flap being configured to unfold without cutting the sleeve so as to facilitate removal of the removable sleeve from the implantable sling.

2. The sling assembly of claim 1, wherein the implantable sling has a looped portion.

3. A protective sleeve for an implantable supportive sling, the protective sleeve comprising:
   a top layer;
   a bottom layer;
   a first longitudinal edge; and
   a second longitudinal edge,
   the top layer including:
      a first portion having a first longitudinally extending discontinuity and a first plurality of transversely extending discontinuities defining a first flap that is anchored and pivots on one of the first longitudinal edge and the second longitudinal edge; and
      a second portion having a second longitudinally extending discontinuity and a second plurality of transversely extending discontinuities defining a second flap that is anchored and pivots on one of the first longitudinal edge and the second longitudinal edge;
   the bottom layer including an intermediate section that is disposed between, and defines a gap between, the first portion of the top layer and the second portion of the top layer,
   the bottom layer, the first flap and the second flap being configured to removably receive the implantable supportive sling.

4. The protective sleeve of claim 3, wherein the first flap is anchored and pivots on the first longitudinal edge, the first longitudinally extending discontinuity and the first plurality of transversely extending discontinuities further defining a third flap that is anchored and pivots on the second longitudinal edge.

5. The protective sleeve of claim 3, wherein the second flap is anchored and pivots on the first longitudinal edge, the second longitudinally extending discontinuity and the second plurality of transversely extending discontinuities further defining a third flap that is anchored and pivots on the second longitudinal edge.

6. The protective sleeve of claim 4, wherein the first longitudinally extending discontinuity and the second longitudinally extending discontinuity are located between the first and second longitudinal edges in the top layer.

7. The protective sleeve of claim 6, wherein each discontinuity of the first plurality of transversely extending discontinuities and the second plurality of transversely extending discontinuities extends between the first longitudinal edge and the second longitudinal edge.

8. The protective sleeve of claim 3, wherein the bottom layer includes a first end tab at a first end of the sleeve and a second end tab at a second end of the sleeve.

9. The protective sleeve of claim 8, wherein the first end tab and the second end tab each comprises at least one through aperture for associating with a delivery device.

10. The protective sleeve of claim 8, wherein the first end tab and the second end tab each comprises a plurality of through apertures, each of which is suitable for associating with a delivery device.

11. The protective sleeve of claim 3, comprising a center tab located near a midpoint of the bottom layer of the sleeve, wherein the center tab encloses a middle section of the bottom layer of the sleeve.

12. The protective sleeve of claim 11, wherein the center tab is heat sealed.

13. The protective sleeve of claim 11, wherein the center tab is clipped.

14. The protective sleeve of claim 3, wherein the first flap and the second flap each include a tapered end.

15. The protective sleeve of claim 3, wherein the first flap and the second flap each include a straight end.

16. The protective sleeve of claim 3, wherein the protective sleeve is formed from a single sheet of material.

17. The protective sleeve of claim 3, wherein a central portion of the sleeve includes a looped portion.

18. The protective sleeve of claim 17, wherein the looped portion is located at a midpoint of the sleeve.

19. The protective sleeve of claim 17, wherein the looped portion at least partially encloses a looped portion of a sling.

20. The protective sleeve of claim 3, wherein the gap is between about 0.5 cm and about 10 cm.

21. An apparatus comprising:
   an implantable supportive sling; and
   a protective sleeve including:
      a first end tab at a first end of the protective sleeve, the first end tab having a through aperture defined therein that is configured to associate the protective sleeve with a delivery device;
      a second end tab at a second end of the sleeve, the second end tab having a through aperture defined therein that is configured to associate the protective sleeve with the delivery device;
      a first flapped portion having a first flap transversely folded over the implantable supportive sling relative to a longitudinal axis of the protective sleeve, the first flapped portion being adjacent the first end tab;
      a second flapped portion having a second flap transversely folded over the implantable supportive sling relative to the longitudinal axis of the protective sleeve, the second flapped portion being adjacent the second end tab the first flap and the second flap being configured to unfold without cutting the sleeve so as to facilitate removal of the protective sleeve from the implantable supportive sling; and a middle portion disposed between the first flapped portion and the second flapped portion, the middle portion defining a gap between the first flap and the second flap, the first end tab, the second end tab, the first flapped portion, the second flapped portion and the middle portion being linearly arranged along the longitudinal axis of the protective sleeve.

\* \* \* \* \*